(12) United States Patent
Williamson et al.

(10) Patent No.: US 11,723,840 B2
(45) Date of Patent: Aug. 15, 2023

(54) INTRADERMAL INJECTION DEVICE

(71) Applicant: Inovio Pharmaceuticals, Inc., Plymouth Meeting, PA (US)

(72) Inventors: Daniel E. Williamson, Sherwood, OR (US); John R. Marshall, Beaverton, OR (US)

(73) Assignee: Inovio Pharmaceuticals, Inc., Plymouth Meeting, PA (US)

( * ) Notice: Subject to any disclaimer, the term of this patent is extended or adjusted under 35 U.S.C. 154(b) by 791 days.

(21) Appl. No.: 16/664,244

(22) Filed: Oct. 25, 2019

(65) Prior Publication Data

US 2020/0054525 A1 Feb. 20, 2020

Related U.S. Application Data (62) Division of application No. 16/035,259, filed on Jul. 13, 2018, now abandoned, which is a division of application No. 12/824,114, filed on Jun. 25, 2010, now Pat. No. 10,045,911.

(51) Int. Cl.
*A61J 1/20* (2006.01)
*A61M 5/30* (2006.01)
*A61M 5/178* (2006.01)
*A61M 5/20* (2006.01)

(52) U.S. Cl.
CPC .............. *A61J 1/2096* (2013.01); *A61M 5/30* (2013.01); *A61J 1/201* (2015.05); *A61M 5/1782* (2013.01); *A61M 5/2033* (2013.01); *A61M 2005/202* (2013.01)

(58) Field of Classification Search
CPC .......... A61M 2005/202; A61M 5/1782; A61M 5/2033; A61M 5/30; A61M 5/3007
See application file for complete search history.

(56) References Cited

U.S. PATENT DOCUMENTS

| | | | | |
|---|---|---|---|---|
| 2,653,602 A * | 9/1953 | Smoot | ...................... | A61M 5/30 91/52 |
| 4,596,556 A * | 6/1986 | Morrow | ................... | A61M 5/30 604/70 |
| 4,623,332 A * | 11/1986 | Lindmayer | .............. | A61M 5/30 604/68 |
| 4,850,967 A * | 7/1989 | Cosmai | .................... | A61M 5/30 604/134 |
| 4,940,460 A * | 7/1990 | Casey, I | ................... | A61M 5/30 604/131 |
| 5,569,189 A | 10/1996 | Parsons | | |
| 5,873,872 A | 2/1999 | Thibault et al. | | |
| 6,123,684 A * | 9/2000 | Deboer | .................... | A61M 5/30 604/134 |
| 8,617,099 B2 * | 12/2013 | Williamson | ............. | A61M 5/30 604/110 |
| 10,045,911 B2 * | 8/2018 | Williamson | ............. | A61M 5/30 |

(Continued)

*Primary Examiner* — Quynh-Nhu H. Vu
(74) *Attorney, Agent, or Firm* — BakerHostetler (57) ABSTRACT

Embodiments herein relate to the field of injections, for instance needle-free injections, and more specifically, to methods and apparatus for spring-driven intramuscular and intradermal injections. Provided in some embodiments are needle-free injectors adapted to deliver intradermal injections, as well as vial adaptors that are adapted to function as spacers when used with a needle-free injection device.

12 Claims, 5 Drawing Sheets

(56) References Cited

U.S. PATENT DOCUMENTS

| | | | |
|---|---|---|---|
| 2002/0151839 A1* | 10/2002 | Landau | A61M 5/30 604/68 |
| 2005/0209553 A1* | 9/2005 | Landau | A61M 5/30 604/72 |
| 2005/0273048 A1* | 12/2005 | Landau | A61M 5/30 604/68 |
| 2006/0089593 A1* | 4/2006 | Landau | A61M 5/30 604/110 |
| 2007/0118094 A1 | 5/2007 | Bingham et al. | |
| 2009/0137949 A1 | 5/2009 | Landau et al. | |
| 2009/0247940 A1 | 10/2009 | Williamson et al. | |
| 2010/0076374 A1 | 3/2010 | Landau et al. | |

* cited by examiner

INTRADERMAL INJECTION DEVICE

CROSS REFERENCE TO RELATED APPLICATIONS

This application is a divisional of U.S. patent application Ser. No. 16/035,259, filed Jul. 13, 2018, which is a divisional of U.S. patent application Ser. No. 12/824,114, filed Jun. 25, 2010, now U.S. Pat. No. 10,045,911, issued on Aug. 14, 2018, the entire contents of which are incorporated herein by reference.

TECHNICAL FIELD

Embodiments herein relate to the field of injections, for instance needle-free injections, and more specifically, to methods and apparatus for spring-driven intramuscular and intradermal injections.

BACKGROUND

Needle-free injection systems provide an alternative to standard fluid delivery systems, which generally use a needle adapted to penetrate the outer surface of a target. Typically, needle-free injection systems are designed to eject the fluid from a fluid chamber with sufficient pressure to allow the fluid to penetrate the target to the desired degree. For example, common applications for needle-free injection systems include delivering intradermal, subcutaneous, and intramuscular injections into or through a recipient's skin. For each of these applications, the fluid must be ejected from the system with sufficient pressure to allow the fluid to penetrate the tough exterior dermal layers of the recipient's skin.

Intradermal injections, the least invasive of the three types, typically are employed when the injectate dose is very small or when visualization of the subject's local response to the injectate is desired. Subcutaneous injections typically are employed when prolonging the absorption time of the medication is desirable, when the dose is relatively small, or when the injectate is non-irritating. Intramuscular injections, the most invasive of the three types, typically are employed when rapid absorption is desired, when the medication is irritating, or when the dose is relatively large.

The efficacy of delivering a needle-free injection to a desired layer of the skin, subcutaneous tissues, or muscle may depend not only on the pressure with which fluid is ejected from the device, but also on the distance of the spray nozzle from the skin. For instance, whereas intramuscular injections typically require the nozzle to be placed directly against the skin to achieve the desired depth of penetration, intradermal injections typically require the use of a spacer between the nozzle and the skin surface. Additionally, the propulsion mechanism employed in many needle-free injector systems involves compressed gas. Such systems require the compressed gas to be replenished when depleted.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF ILLUSTRATIVE EMBODIMENTS

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order-dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "NB" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Figure 1:
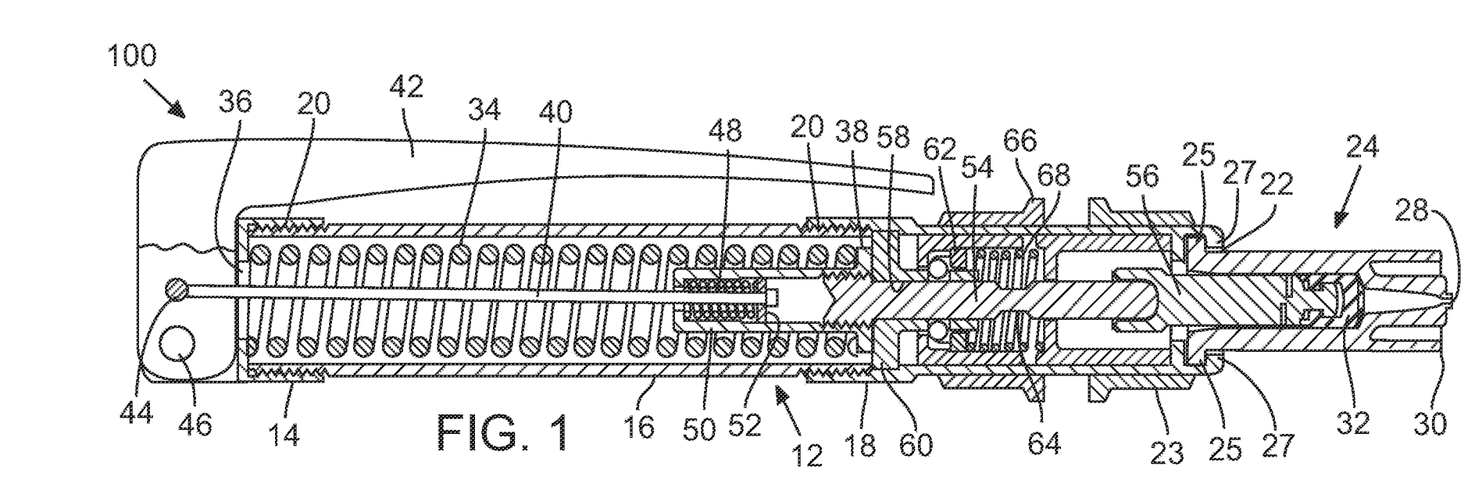
FIG. 1 is a side elevation, sectional view of an embodiment of an injector pen in a "fired" state, in accordance with various embodiments.

In various embodiments, needle-free injector methods, apparatuses, and systems are provided. FIG. 1 illustrates an example of a needle-free injection device 100. Device 100 may include a body 12 to enclose various systems used to effect an injection. Body 12 typically is sized and shaped to be held comfortably in a user's hand and may take any suitable configuration. In some embodiments, body 12 may be formed from injection-molded plastic, although various other materials and fabrication methods also may be suitable.

As illustrated in FIG. 1, body 12 may be comprised of various subsections, such as housings 14, 16, and 18. Housings 14, 16, and 18 may be configured to couple to one another, for instance by threaded connectors 20, or by any other suitable connecting mechanisms, such as snap locks.

In various embodiments, body 12 may include an opening 22 in an end of the device 100 that may be adapted to receive a nozzle assembly 24. Body 12 also may include other apertures, such as one or more view ports, for instance to provide feedback or instructions to a user of the device. In some embodiments, the apertures may align with indicia, such as arrows or text, which instruct a user in proper operation of the device or convey information to a user, such as the current configuration or status of the device.

Figure 2:
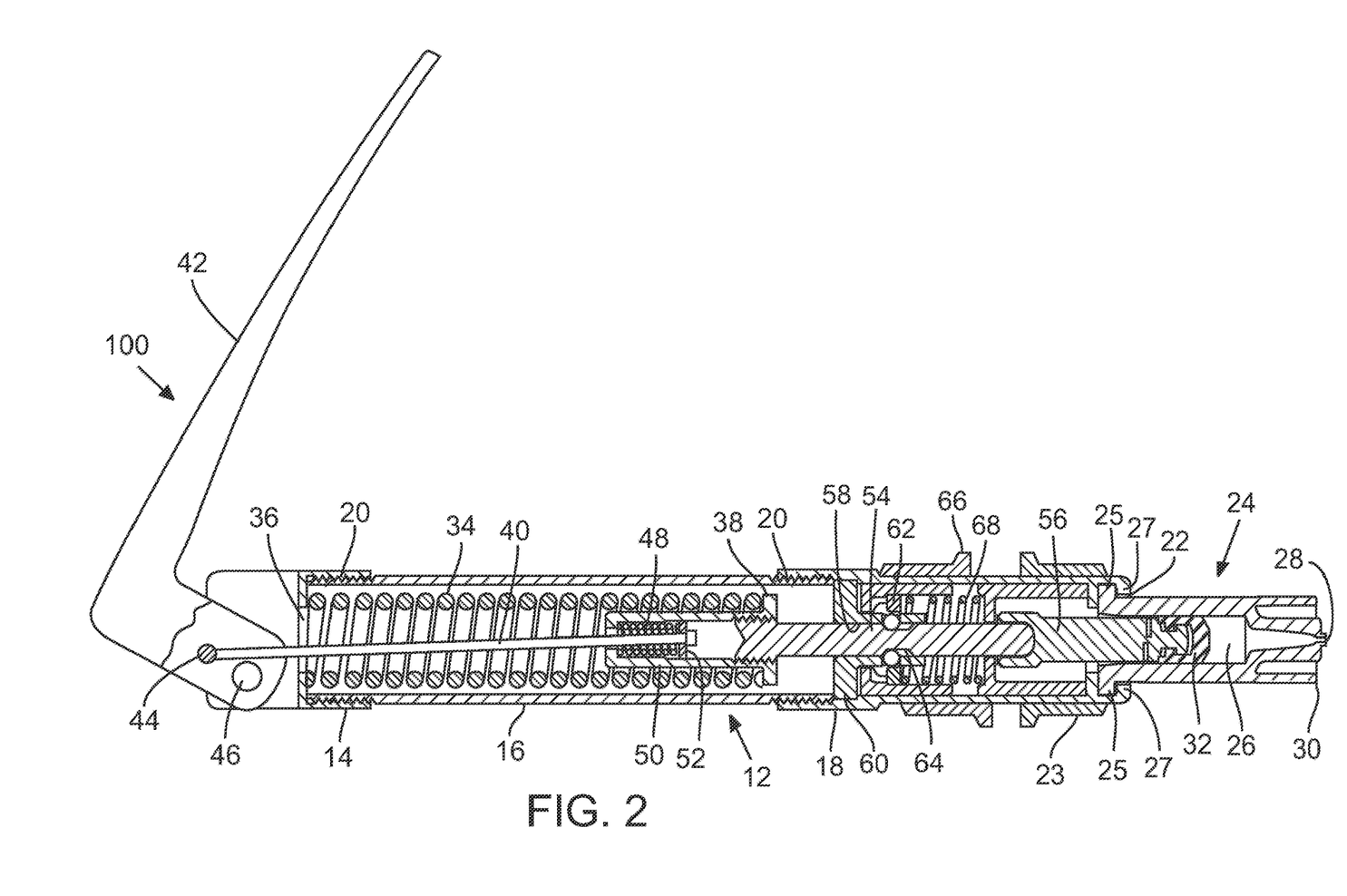
FIG. 2 is a side elevation, sectional view of an embodiment of an injector pen in an "arming" state, in accordance with various embodiments.

In various embodiments, nozzle assembly 24 may be configured to be selectively coupled to an injection mechanism. Turning to FIG. 2, nozzle assembly 24 may include an injectate chamber 26 adapted to accommodate a volume of injectate, and an outlet orifice 28 through which the injectate is ejected from device 100. In some embodiments, nozzle assembly 24 also may provide an interface with a recipient's skin. For instance, in some embodiments, nozzle assembly 24 may include a skin tensioning ring 30, which may help pull the skin taught during an injection procedure. Skin tensioning ring 30 may be particularly useful when device 100 is used to administer an intramuscular injection. Nozzle assembly 24 may further include a plunger 32 configured to move through injectate chamber 26 toward outlet orifice 28 to expel an injectate. Nozzle assembly 24 also may include a tapered Luer connector, for instance for coupling to a spacer device. Such spacer devices are discussed in greater detail below, and may be particularly useful when using device 100 to administer an intradermal injection. In various embodiments, nozzle assembly 24 may remain seated in the opening 22 of device 100 until released by sliding latch member 23 in a direction away from nozzle assembly 24.

Figure 6A:
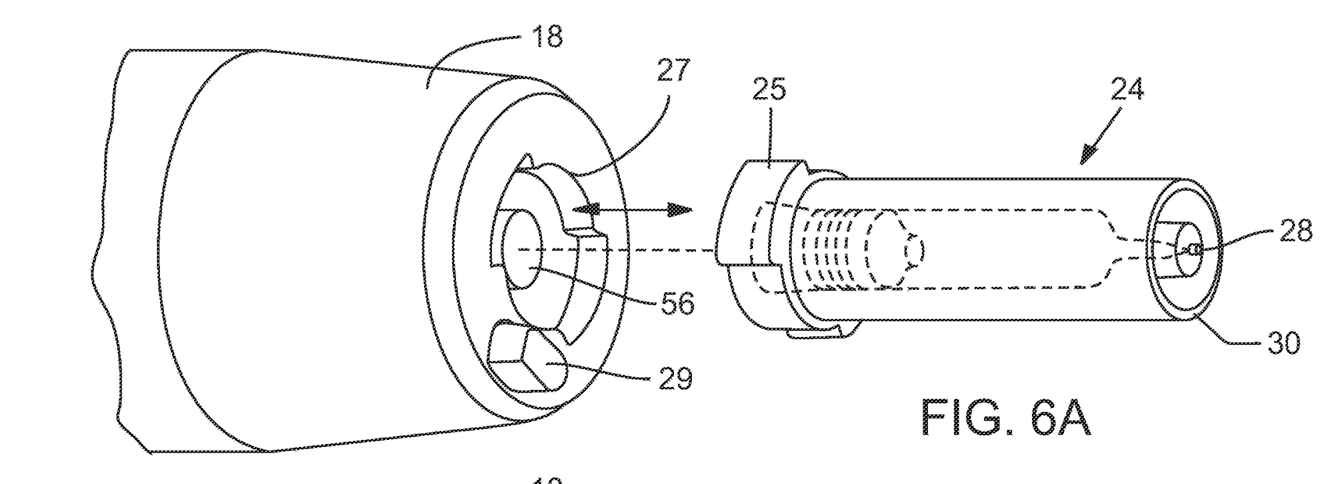
FIGS. 6A and 6B are side elevation views of an embodiment of a nozzle adapted to fit into an aperture of an injector pen.
Figure 6B:
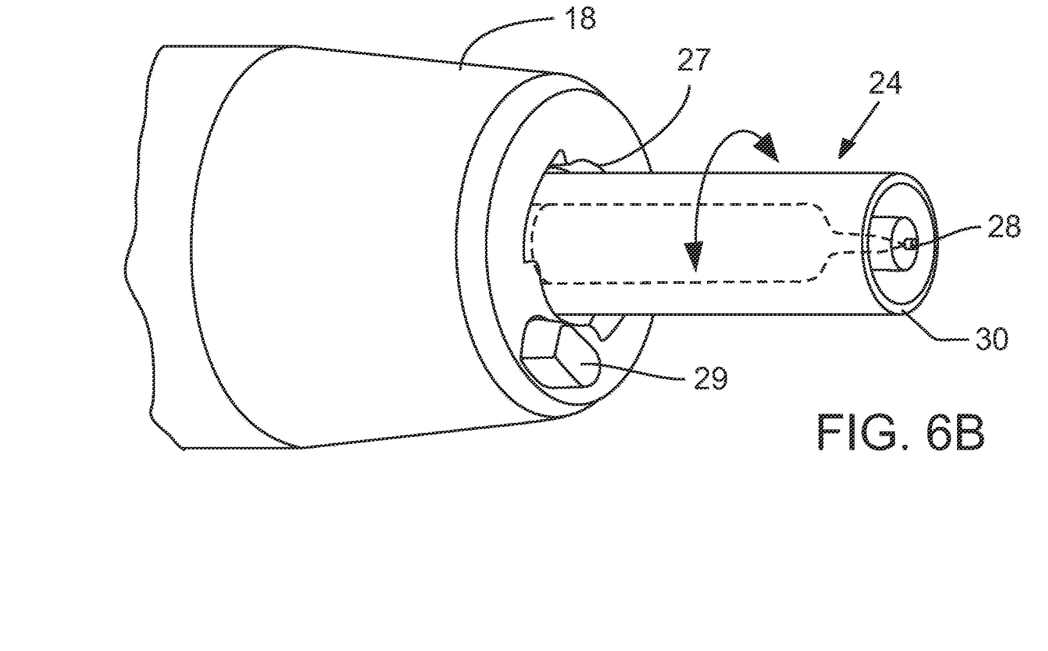

FIGS. 6A and 6B, show an alternate embodiment of the device, in which nozzle assembly 24 may couple to the opening 22 via flanges 25 that may fit within notches in a flange retainer 27 adjacent opening 22. As shown, rotation of nozzle assembly 24 may couple and decouple nozzle assembly 24 from opening 22. In some embodiments, nozzle assembly 24 may lock into position when seated in flange retainer 27, and may be released by actuation of release button 29.

Device 100 includes one or more systems to effect an injection. For example, turning once again to FIG. 1, the illustrated embodiment shows an example of device 100 in a "fired" state (e.g., device 100 has not been armed or cocked in this illustration). In various embodiments, housed within body 12 is a drive source, such as a spring 34, disposed between spring stop members 36, 38, such that bringing spring stop members 36, 38 closer together compresses spring 34, and decompressing spring 34 pushes stop members 36, 38 away from one another. Spring stop member 38 is typically coupled to a rod 40 that may extend beyond spring stop member 36 to couple to lever 42 at attachment point 44. As illustrated in FIG. 2, which depicts device 100 in an "arming" state, device 100 may be armed or cocked by pivoting lever 42 at hinge 46. Pivoting lever 42 about hinge 46 results in tension on rod 40, which is transmitted to stop member 38, to move stop member 38 toward stop member 36, thereby compressing spring 34. Lever 42 is normally returned to its original position by tension on rod 40 provided by small spring like that depicted at 48. Small spring 48 is typically housed within a slotted link 50, which may be a component of stop member 38. In some embodiments, pivoting lever 42 about hinge 46, in addition to compressing spring 34, also may compress small spring 48 between slotted link 50 and spring stop member 52, which may be coupled to the end of rod 40. Small spring 48 typically applies sufficient force on lever 42 to return lever 42 to a home position, as shown in the FIG. 3 "armed" position.

In the depicted embodiment, stop member 38 is coupled to shaft member 54, which is in turn coupled to (or in contact with) plunger member 56, which is shown to be coupled to plunger 32. In some embodiments, shaft member 54 may make contact with plunger member 56, whereas in other embodiments, shaft member 54 may be physically coupled to plunger member 56, for instance with a threaded coupling or the like. Thus, pivoting lever 42 about hinge 46 results in the compression of spring 34 and the sliding of shaft member 54 (which is shown to be coupled to stop member 38) through a channel 58 in anchor member 60. In the depicted embodiment, this sliding of shaft member 54 moves plunger member 56 and plunger 32 away from outlet orifice 28. In other embodiments, such as when shaft member 54 is not coupled to plunger member 56, plunger 32 may be moved away from outlet orifice 28 prior to insertion in the device 100. For instance, this may be the case when pre-filled nozzle assemblies are used.

Figure 7A:
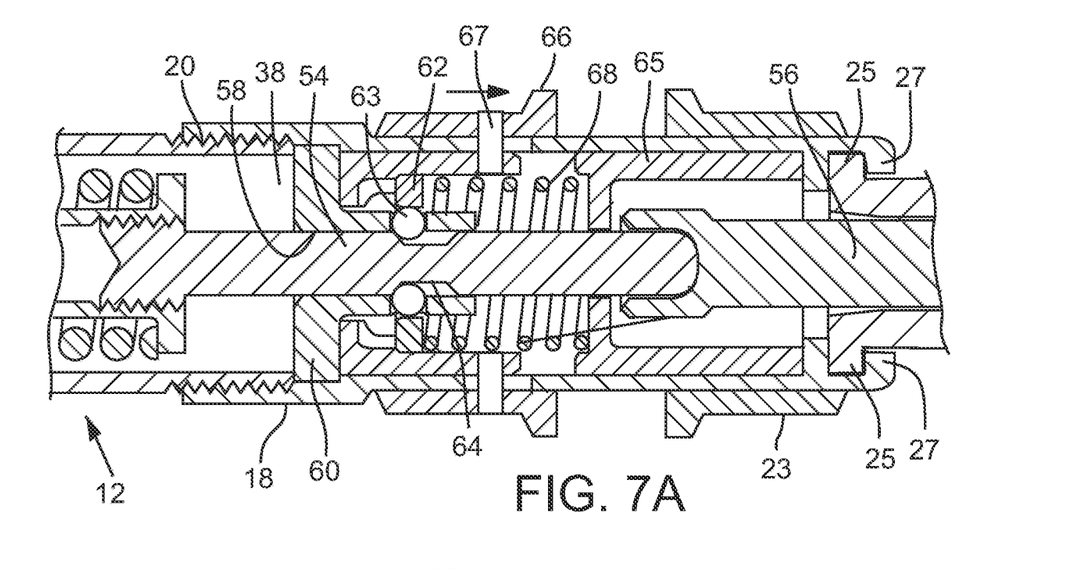
FIGS. 7A and 7B are close-up side elevation, sectional views of a retaining mechanism adapted to retain a plunger in an armed position (7A) until it is released by a trigger mechanism (7B), in accordance with various embodiments.
Figure 7B:
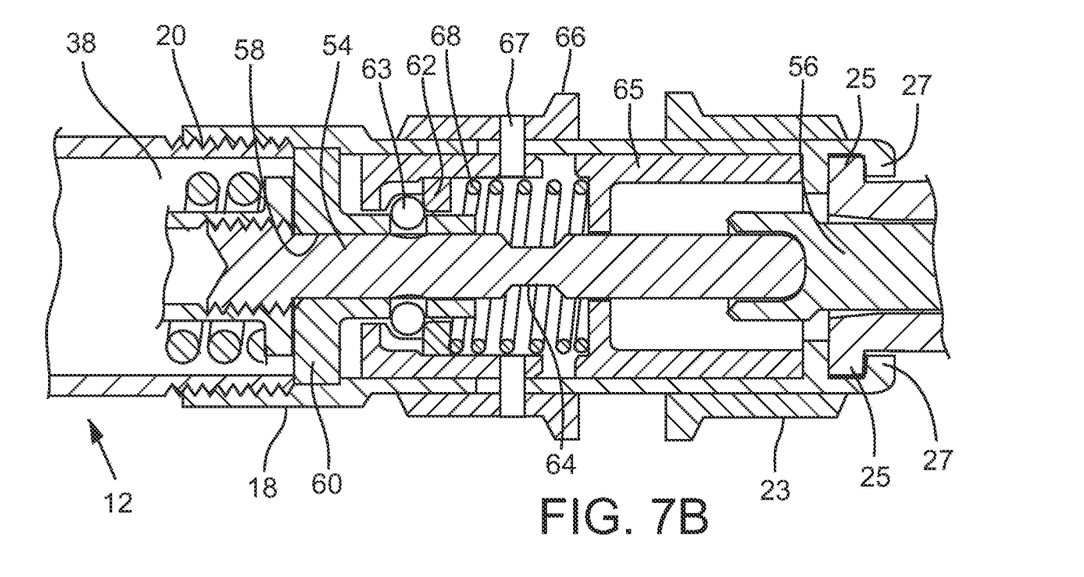

As shown in FIGS. 7A and 7B, once device 100 is cocked or armed, ball bearings 63 or other retention members may be forced out of their home positions by slide bushing 62 and into a notch 64 in shaft member 54, where they may retain shaft 54 in the cocked or armed position. In some embodiments, tension may be applied to both slide bushing 62 and front base 65 by spring 68, which also provides tension against latch members 66 and 23 and bearings 63.

Thus, to load device 100 with injectate, for instance in preparation for administering an injection, a user may simply place the outlet orifice 28 in contact with an injectate fluid, and pivot lever 42 about hinge 46 as shown in FIG. 2. In various embodiments, this action will create a vacuum in injectate chamber 26, and injectate will be drawn into injectate chamber 26 via outlet orifice 28. In various embodiments, device 100 will remain in the cocked or armed position until actuated by a user.

Figure 3:
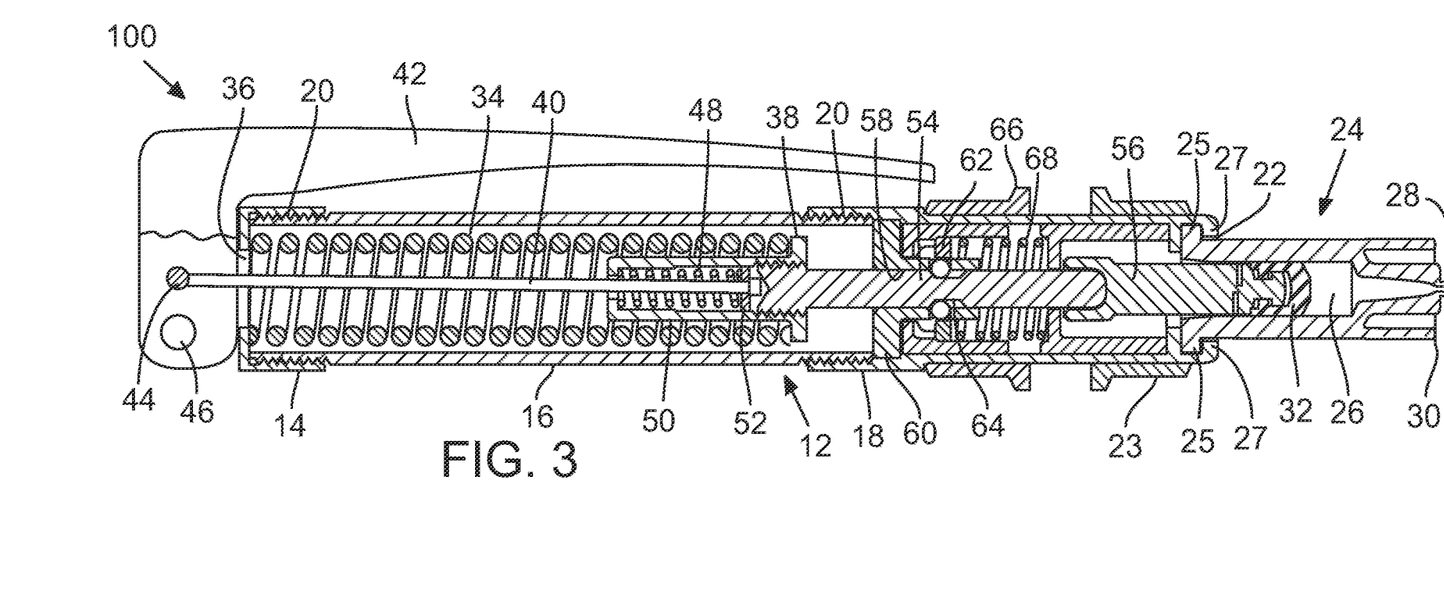
FIG. 3 is a side elevation, sectional view of an embodiment of an injector pen in an "armed" state, in accordance with various embodiments.

FIG. 3 illustrates an embodiment of the device 100 in a cocked or armed state, ready to be used to administer an injection. In use, outlet orifice 28 may be placed in contact with or adjacent to the skin of a subject in a desired location. In the depicted embodiment, pressure exerted on latch member 66 in the direction of the nozzle assembly and the patient receiving the injection will compress spring 68 against front base 65, releasing the ball bearings 63 from notch 64 and allowing spring 34 to propel shaft member 54, plunger member 56, and plunger 32 towards outlet orifice 28, returning them to their respective home positions as shown in FIG. 1. Plunger member 56 would expel injectate from injectate chamber 26 during this process, through output orifice 28, and into the body of the patient.

Thus, the disclosed injection devices 100 are configured to expel a volume of fluid, such as a drug. The word "drug" as used herein is intended to encompass, for example, and without limitation, any medication, pharmaceutical, therapeutic, vaccine, aesthetic, or other material which may be administered by injection.

In some embodiments, plunger 32 may be at least partially visible through the nozzle assembly 24 body. Plunger 32 may include first and second visibly distinct regions such that movement of the plunger 32 through the nozzle assembly 24 is measurable. For example, plunger 32 may include an over-molded tip in some embodiments, so that the tip is visibly distinct from the rest of the proximal portion of the plunger 32. In other configurations, the proximal portion may be visibly distinct from the distal portion of plunger 32. In some embodiments, injectate chamber 26 may include a dose scale to incrementally measure the volume of the injectate drawn into the chamber. In some versions of device 100, the dose scale may include indicia and the first and second visibly distinct regions of the plunger may be configured to align with the indicia. Additionally or alternatively, the dose scale may be a pre-molded dose scale having ribs to indicate each unit of measure. Additionally, one or more dosage spacers may be included in any of various points along the shaft member 54 and/or plunger member 56 in order to vary the volume of injectate drawn into the injectate chamber 26 when the device is loaded.

Some embodiments may include a system to prevent nozzle assembly 24 from being re-filled. U.S. Patent Application 2010/0076374 is incorporated herein by reference, and includes an auto-disabled plunger that includes a frangible section to provide additional protection so the cartridge cannot be re-used. Two other systems that may be used to prevent reuse of the nozzle assemblies are known as the B-2000 device and the Zetajet system. The B-2000 device has a proprietary nozzle attachment system consisting of three lugs on the nozzle that fit through three matching cutouts in the front cover of the B-2000 device. In embodiments, the nozzle may lock into place by inserting the nozzle into the device through the three cutouts, then rotating the nozzle approximately 60° where it bears on the front cover between the cutouts. There is a spring loaded detent within the device that provides feedback to the user when the nozzle is in its final locked position.

In various embodiments, the plunger for the B-2000 nozzle protrudes from the nozzle, but does not contact any portion of the B-2000 when the nozzle and plunger are inserted into the B-2000 device. In some embodiments, the B-2000 also may have an auto-disable feature. When the B-2000 is fired, grippers within the B-2000 that are arranged radially around the plunger may grab the protruding portion of the plunger then force the plunger forward throughout the injection sequence.

The Zetajet device has a proprietary nozzle attachment system consisting of two lugs on the nozzle that fit through two matching cutouts in the front cover of the Zetajet device. The nozzle locks into place by inserting the nozzle into the device with the lugs oriented to fit through the two cutouts, then rotating the nozzle 90° where it bears on the front cover between the cutouts. In embodiments, there is a spring-loaded component within the device that both locks the nozzle into place and provides feedback to the user when the nozzle is in its final locked position.

In embodiments, the Zetajet nozzle may have a plunger tip that is set in place within the nozzle. In some examples, it is set into its final position when the nozzle is filled. The Zetajet device has a ram component in contact with the power spring that comes into close contact with the plunger tip when the nozzle is inserted. When the device is triggered, the ram is driven forward, pushing on the plunger tip driving the fluid out of the nozzle.

Figure 4:
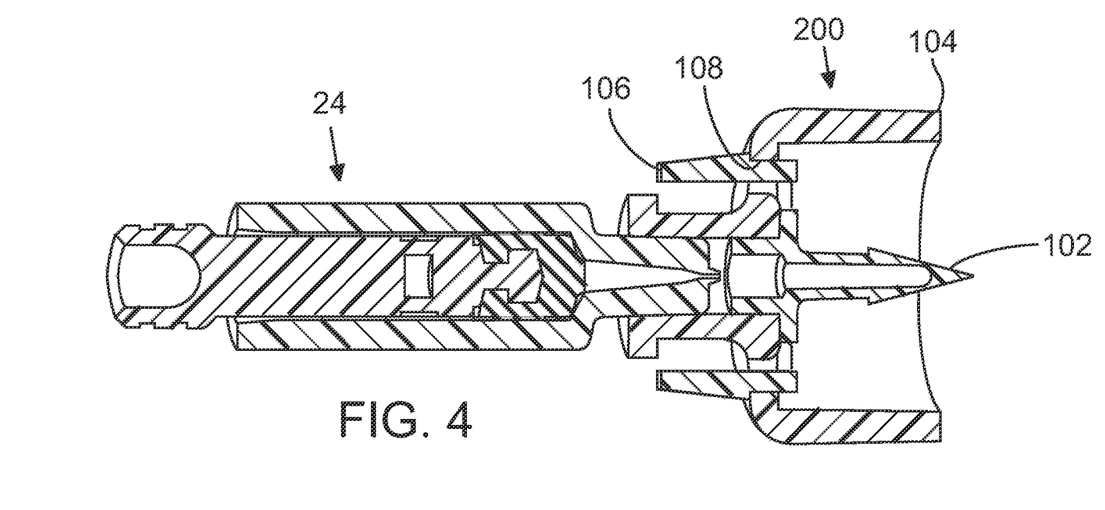
FIG. 4 is a side elevation, sectional view of an embodiment of a nozzle with an adapter for use with an injector pen, in accordance with various embodiments.
Figure 5:
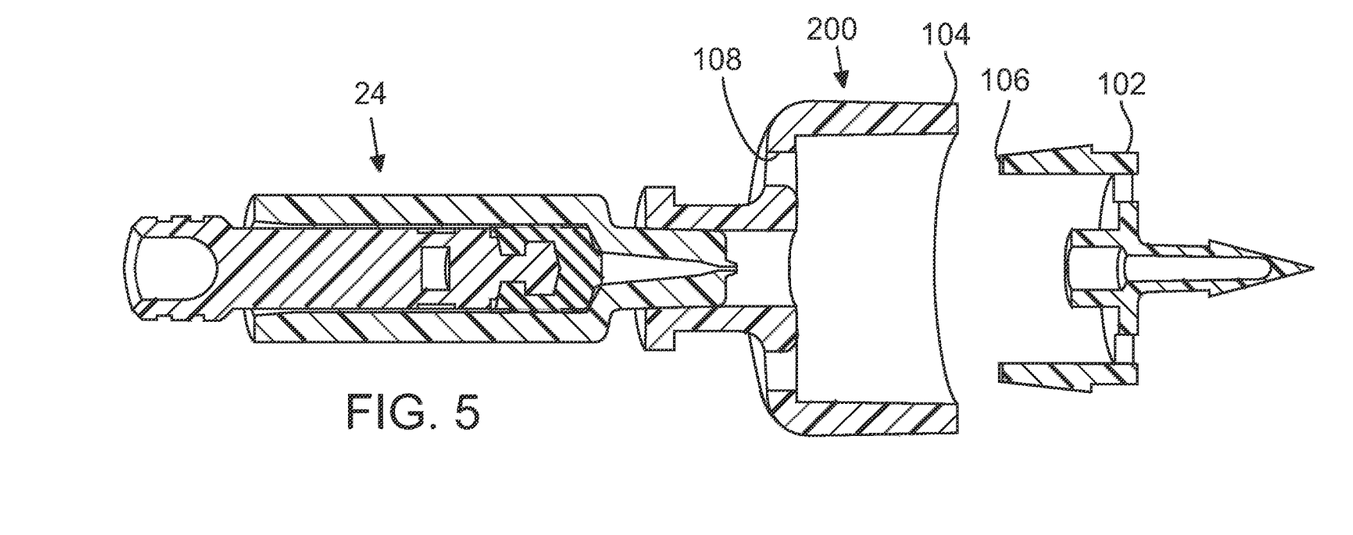
FIG. 5 is a side elevation, sectional view of an embodiment of the same nozzle with the adapter removed, in accordance with various embodiments.

FIGS. 4 and 5 illustrate examples of a vial adapter 200 that may engage the nozzle assembly 24 (for instance, by coupling to the Luer connector 30) to couple the nozzle assembly 24 to a vial of injectate during loading of the nozzle assembly 24. The vial adapter may include a break-away spike component 102 that is typically adapted to penetrate the rubber seal on a drug vial during loading of the injector device 100. In addition, vial adapter 200 may include a flange 104 that is adapted to fit around the cap of a drug vial. In use, vial adapter 200 may be aligned with the vial cap, and downward pressure may be applied until spike component 102 penetrates through the vial seal, forming a sealed fluid conduit between device 100 and the vial.

In various embodiments, break-away spike component 102 may be coupled to vial adaptor 200 by one or more flexible tabs 106 adapted to be disposed in apertures 108. Once seated, in the depicted embodiment flexible tabs 106 hold the spike component 102 in place with spring tension. As shown in FIG. 5, squeezing flexible tabs 106 permits decoupling of the spike component from the vial adaptor. Once the spike component 102 has been removed from the vial adapter 200, the adapter 200 may serve as a spacer device, for instance for use in administering intradermal injections. In some embodiments, the spacer device provides about ½ inch of clearance between the outlet orifice 28 and the skin. In particular, non-limiting examples, the outlet orifice 28 will typically be 0.055" or 0.062".

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed:

1. A method of using a needle-free injection device, the needle-free injection device comprising: a body terminating in a nozzle; a fluid reservoir housed within the body and adapted to receive a fluid injectate; a plunger disposed within the fluid reservoir; a shaft to which the plunger is mounted such that when the shaft is driven forward, the plunger is responsively driven forward; and a spring-driven propulsion system having a first spring; the method comprising:

pivoting a lever relative to the body to tension a rod extending between the lever and the shaft, wherein tensioning the rod compresses the first spring and causes at least one retention member to be forced into a notch in the shaft, thereby retaining the shaft in an armed position;

biasing the lever via a second spring towards a home position; and releasing the at least one retention member from the notch, thereby expanding the first spring and propelling the shaft and plunger toward the nozzle, thereby expelling fluid injectate from the fluid reservoir through the nozzle.

2. The method of claim 1, wherein pivoting the lever to tension the rod comprises moving a handle portion of the lever away from the body, and biasing the lever via the second spring towards the home position comprises moving the handle portion of the lever towards the body.

3. The method of claim 2, wherein the second spring resides within a slotted link, and biasing the lever via the second spring towards the home position comprises expanding the second spring within the slotted link, thereby moving a spring stop member that couples the second spring to the rod toward the nozzle.

4. The method of claim 1, further comprising, before releasing the at least one retention member from the notch, filling the fluid reservoir with the fluid injectate.

5. The method of claim 4, wherein filling the fluid reservoir comprises:
coupling a vial connector to the nozzle, wherein the vial connector includes a removable spike connector;
coupling a drug vial containing the fluid injectate to the vial connector, such that the removable spike connector penetrates a septum of the drug vial,
wherein pivoting the lever to tension the rod moves the plunger away from the nozzle and draws the fluid injectate from the drug vial, through the nozzle, and into the fluid reservoir, thereby filling the fluid reservoir with the fluid injectate;
decoupling the drug vial from the vial connector; and
decoupling the spike connector from the vial connector.

6. The method of claim 1, wherein the first spring exerts a bias force on the shaft towards the nozzle, and tensioning the rod causes the rod to transmit a load force between the lever and the shaft so as to load the first spring, wherein the load force is opposite the bias force.

7. The method of claim 1, wherein pivoting the lever to tension the rod comprises moving a handle portion of the lever away from the body, and biasing the lever via the second spring towards the home position comprises moving the handle portion of the lever towards the body.

8. The method of claim 1, wherein the notch is at a mid-section of the shaft, and the at least one retention member comprises ball bearings, wherein tensioning the rod forces the ball bearings into the notch, and a slide bushing is biased by another spring so as to hold the ball bearings within the notch.

9. The method of claim 8, wherein releasing the at least one retention member comprises moving a latch member, which compresses the another spring and moves the slide bushing, thereby releasing the ball bearings from the notch.

10. The method of claim 1, further comprising, before releasing the at least one retention member from the notch, filling the fluid reservoir with the fluid injectate.

11. The method of claim 10, wherein filling the fluid reservoir comprises:
coupling a vial connector to the nozzle; and
coupling a drug vial containing the fluid injectate to the vial connector,
wherein pivoting the lever to tension the rod moves the plunger away from the nozzle and draws the fluid injectate from the drug vial, through the nozzle, and into the fluid reservoir, thereby filling the fluid reservoir with the fluid injectate.

12. The method of claim 11, further comprising:
decoupling the drug vial from the vial connector before releasing the at least one retention member from the notch.

\* \* \* \* \*